United States Patent [19]
Folkers et al.

[11] Patent Number: 4,481,139
[45] Date of Patent: Nov. 6, 1984

[54] PEPTIDE ANTAGONISTS OF SUBSTANCE P

[75] Inventors: Karl Folkers, Austin, Tex.; Xu Jie-cheng, Shanghai, China

[73] Assignee: Board of Regents, The University of Texas System, Austin, Tex.

[21] Appl. No.: 484,646

[22] Filed: Apr. 13, 1983

[51] Int. Cl.$^3$ ............................................. C07C 103/52
[52] U.S. Cl. ............................................... 260/112.5 R
[58] Field of Search ................................. 260/112.5 R

[56] References Cited
PUBLICATIONS

Chem. Abstr. vol. 91, (1979) 193630R.

Primary Examiner—Delbert R. Phillips
Attorney, Agent, or Firm—Arnold, White & Durkee

[57] ABSTRACT

Undecapeptides retaining the amino acids in positions 2, 3, 4, 5, 6, 8 and 10 of substance P (Arg$^1$-Pro$^2$-Lys$^3$-Pro$^4$-Gln$^5$-Gln$^6$-Phe$^7$-Phe$^8$-Gly$^9$-Leu$^{10}$-Met$^{11}$-NH$_2$), but having substitutions in positions 1, 7, 9 and 11 of substance P have been discovered to have high antagonistic activity to block substance P in biological systems. Exemplifying these potent antagonists is D-Arg$^1$,D-Trp$^7$,D-Trp$^9$, Leu$^{11}$-Substance P, which is an effective inhibitor and has high potency. These antagonists of substance P are useful to elucidate some biological mechanisms of substance P, and to treat inflammatory responses in the eye for medical practice in ophthalmology, and to be novel analgesic agents for medical applications.

7 Claims, No Drawings

PEPTIDE ANTAGONISTS OF SUBSTANCE P

BACKGROUND OF THE INVENTION

The sequence-biological activities of the luteinizing hormone releasing hormone (LHRH) (Glp-His-Trp-Ser-Tyr-Gly-Leu-Arg-Pro-Gly-$NH_2$) and substance P (SP) (Arg-Pro-Lys-Pro-Gln-Gln-Phe-Phe-Gly-Leu-Met-$NH_2$) differ in an important structural aspect. No truncated analog of LHRH is known which has activity equal to that of LHRH. Although LHRH is a decapeptide and SP is an undecapeptide, the removal of the N-terminal four or five amino acids of SP gives truncated hexa- and heptapeptides which show biological activities essentially equivalent ot that of SP itself. For example, the studies of Yanaihara et al. ["Substance P Nobel Symposium 37", U.S. von Euler and B. Pernow, eds., Raven Press, New York (1977) p. 27] exemplify data on sequence-activity of truncated analogs of SP, which showed that the hexapeptide, Glp-Phe-Phe-Gly-Leu-Met, and the heptapeptide, Glp-Gln-Phe-Phe-Gly-Leu-Met-$NH_2$, showed 2.0 and 1.7 relative activities, respectively, in comparison with SP as 1.

It is generally believed in the field of SP that the N-terminal $Arg^1$-$Pro^2$-$Lys^3$-$Pro^4$- or $Arg^1$-$Pro^2$-$Lys^3$-$Pro^4$-$Gln^5$- of SP are not needed for biological activity and such statements imply the concept that these N-terminals four or five amino acids have no biological role whatsoever. This concept may not be entirely correct, because it is possible that these four or five N-terminal amino acids of SP have a role in binding at one or more receptors, particularly when one considers the strong functionality of $Arg^1$ and $Lys^3$ in these units. Also, the presence of $Pro^2$ and $Pro^4$ indicate a unique conformational contribution from the N-terminal portion of SP. Therefore, the presence of $Arg^1$-$Pro^2$-$Lys^3$-$Pro^4$- and $Arg^1$-$Pro^2$-$Lys^3$-$Pro^4$-$Gln^5$- should not be summarily dismissed from consideration of some nature of a biological role.

Doubtless, peptide chemists, in general, were attracted to synthesize truncated analogs of SP not only because the N-terminal moiety does not contribute to agonist mechanisms, but because truncated analogs can be more quickly synthesized, and at less expense, and probably be purified to a high state of purity more readily than the corresponding undecapeptides.

We have investigated truncated analogs of SP as antagonists in comparison with the corresponding undecapeptides. In doing so, we have surprisingly discovered certain undecapeptides which have higher antagonistic activity than any previously known analog of SP. We have also discovered that a certain truncated analog has substantially less antagonistic activity than that of the corresponding undecapeptide. This finding that a potent undecapeptide has substantially more antagonistic activity than a corresponding truncated peptide is not in agreement with the comparable agonistic activities of truncated analogs of substance P.

THE INVENTION

It has been discovered, in accordance with the present invention, that undecapeptides having $Pro^2$-$Lys^3$-$Pro^4$-$Gln^5$-$Gln^6$-$Phe^8$-$Leu^{10}$ as does substance P, but have substitutions in positions 1, 7, 9 and 11, such as [D-$Arg^1$,D-$Trp^7$,D-$Trp^9$,$Leu^{11}$]-SP have exceptional antagonistic activity and greater than that of any previously described analog of substance P; in addition, it has been surprisingly discovered that the truncated analog, which is [$GlP^5$,D-$Trp^7$,D-$Trp^9$,$Leu^{11}$]-$SP_{5-11}$, of this exceptionally potent antagonist is substantially less active than its corresponding undecapeptide, [D-$Arg^1$,D-$Trp^7$,D-$Trp^9$,$Leu^{11}$]-SP.

The exceptional antagonistic activity of [D-$Arg^1$,D-$Trp^7$,D-$Trp^9$,$Leu^{11}$]-SP makes this peptide very useful, over and above previous peptides, such as [D-$Pro^2$,D-$Trp^7$,D-$Trp^9$]-SP. [D-$Arg^1$,D-$Trp^7$,D-$Trp^9$,$Leu^{11}$]-SP is substantially more potent than [D-$Pro^2$,D-$Trp^7$,D-$Trp^9$]-SP, and is more useful to alleviate inflammatory symptoms in the eye, according to medical practice is ophthalmology, particularly since topical application is sufficient to reduce inflammation.

This remarkably attractive antagonist was synthesized by solid-phase experimentation. The deprotection and cleavage of the undecapeptide from the resin was accomplished by hydrogen fluoride and the resulting peptidic material was purified to yield the pure [D-$Arg^1$,D-$Trp^7$,D-$Trp^9$,$Leu^{11}$]-SP.

GENERAL METHODS

The acquisition is protected amino acids, the synthesis of the peptides, the cleavage of the peptides from the resin, were conducted as described for the previous analogs and antagonists of substance P [K. Folkers, J. Hörig, S. Rosell and U. Björkroth, Acta Physiol. Scand. 111, 505 (1981)].

The modified purification of the crude peptides, as carried out for the peptides described herein, was conducted as follows. Samples of about 200 mg of the crude peptides were applied to a column of Sephadex G-25 (100×2.5 cm) which had been equilibrated with 12% acetic acid, and then chromatography was carried out with the same solvent. Fractions of 10 ml were collected. The peptides were detected by spotting samples of the individual fractions as silica gel plates and conducting the chromatography with n-BuOH:HOAc:$H_2O$=4:1:2. The chromatography was carried out with this same solvent system, and fractions of 4 ml were collected. The desired peptides, in general, were found in fractions 30–40. Those fractions which contained the pure or nearly pure peptide were collected and lyophilized. If the desired peptide were not sufficiently pure, it was again purified over silica gel using the same solvent system. The yields of the peptides were 20–50%. Purity was more important than the yield, and ranged from 90 to 98%, which was acceptable for the first sample for the assay and its error. The time for achievement of purity was balanced with the time of synthesis and assay and the achievement of higher potency of antagonism which was the important goal. The peptidic impurities were not a deterrent toward the goal. High performance liquid chromatography was conducted on a Waters Liquid Chromatograph equipped with a Waters 660 solvent programmer. The samples were chromatographed on a $\mu$-Bondapak $C_{18}$ column (10$\mu$), 3.9×300 mm. For elution of the peptides, a linear gradient from 20–100% of a solvent system was used during 25 min. The solvent system consisted of 70% of $CH_3CN$ and 30% 0.1M K $H_2PO_4$ buffer, pH 3. The flow rate was 2.0 ml/min. and 10 $\mu$l of a 0.1% solution of the peptide was injected. The eluted peptide was detected by its UV absorbance at 206 nm.

EXEMPLARY SYNTHESIS OF [D-Arg$^1$,D-Trp$^7$,D-Trp$^9$,Leu$^{11}$]-SP

The protected amino acids were purchased from Peninsula Laboratories, Inc., San Carlos, Calif. α-Amino functions were protected by the BOC-group. Side-chain functions were protected by o-Cl-Z for α-amino function of Lys, Tos for Arg. The benzhydrylamine hydrochloride resin was obtained from Beckman, Inc., Palo Alto, Calif. All solvents (excepts TFA and isopropanol) were distilled before use. To check homogeneity the peptides were chromatographed on precoated TLC plates (silica gel 60 F-254 E. Merck, Darmstadt, Germany).

The peptides was built up by the stepwise solid-phase manual method on benzhydrylamine hydrochloride resin. The procedure of synthesis was as follows:

Deprotection. (1) CH$_2$Cl$_2$ (wash 2 times, 2 min.); (2) 50% TFA in CH$_2$Cl$_2$ containing 0.1% indole (wash 1 time, 2 min.); (3) 50% TFA in CH$_2$Cl$_2$ containing 0.1% indole (deprotection, 30 min.); (4) CH$_2$Cl$_2$ (wash 3 times, 2 min.).

Neutralization. (1) CH$_2$Cl$_2$ (wash 2 times, 2 min.); (2) 10% Et$_3$N in CH$_2$Cl$_2$ (wash 1 time, 1 min.); (3) 10% Et$_3$N in CH$_2$Cl$_2$ (neutralization, 5 min.); (4) CH$_2$Cl$_2$ (wash 5 times, 2 min.).

DCC Coupling. (1) CH$_2$Cl$_2$ (wash 2 times, 2 min.); (2) amino acid in solution in CH$_2$Cl$_2$ was added (3) 10% DCC in CH$_2$Cl$_2$ was added (at room temperature for 3-6 hr); (4) CH$_2$Cl$_2$ (wash 2 times, 2 min.); (5) DMF (wash 3 times, 2 min.); (6) i-PrOH (wash 2 times, 2 min.); (7) CH$_2$Cl$_2$ (wash 2 times, 2 min.).

Active Ester Coupling. (1) CH$_2$Cl$_2$ (wash 2 times, 2 min.); (2) amino acid solution in DMF and a few mg of 1-hydroxybenzotriazole as a catalyst were added (at room temperature for 6-24 hr); (3) CH$_2$Cl$_2$ (wash 2 times, 2 min.); (4) DMF (wash 2 times, 2 min.); (5) 2-PrOH (wash 3 times, 2 min.); (6) CH$_2$Cl$_2$ (wash 3 times, 2 min.).

Acetylation. (1) CH$_2$Cl$_2$ (wash 2 times, 2 min.); (2) 25% Ac$_2$O and 25% pyridine in CH$_2$Cl$_2$ (acetylation, 20 min.); (3) CH$_2$Cl$_2$ (wash 4 times, 2 min.).

The first amino acid BOC-Leu was attached to the resin 1 g (0.75 mM NH$_2$/g) by the following procedure: neutralization and DCC coupling. Before placing the resin into the 30 ml Funnel Buchner (This funnel was connected with a 250 ml filter flask. The side tube of the filter flask was connected with a water pump only when it was needed for the washing solvent. Whenever the Buchner funnel was used as a reaction container, the side tube of the filter flask was sealed by a rubber bulb for protecting against leakage of the reaction solution). The resin was washed twice in a separate funnel with 25 ml of CH$_2$Cl$_2$/g resin to remove the fine particles. In all couplings, a 4-fold excess of the protected amino acid was used. This procedure generally resulted in a complete coupling. If a positive ninhydrin color was observed, a second coupling was needed with the 4-fold excess of protected amino acid. Then the resin was acetylated. The next amino acid was attached by the following procedure: deprotection, neutralization and DCC coupling or active ester condensation. The volume of the solvents and reagents used for washing and performing chemical reaction was about 10 ml/g resin. The acetylation mixture was freshly prepared before each use.

Cleavage of Peptide from Resin. After all of the amino acids had been coupled, the protected peptide resin was dried overnight, in vacuum, by an oil pump. The resin weighed 2.01 g. The resin containing 10% distilled anisole was treated with double-distilled and dried (over CoF$_3$) liquid hydrogen fluoride (about 25 ml) for 1 hr at 0° C. Then, the HF was evaporated under reduced pressure by a water pump, and the residue was dried overnight, in vacuum, by an oil pump. The mixture was then extracted twice with EtOAc (70 ml) and then twice with 70 ml of 12% HOAc and twice with 15 ml water. The combined aqueous solution was lyophilized to obtain the crude peptide; 1100 ml.

Purification of the Peptide. 1100 mg of the crude peptide was applied on Sephadex G-25 column (100×2.5 cm) which had been equilibrated with 12% HOAc. Elution was with the same solvent. Fractions of 10 ml were collected. Each fraction was tested on silica gel plates with the solvent system n-BuOH:HOAc:H$_2$O=4:1:2. Fractions 36-42 were collected. These combined fractions were lyophilized; 210 mg of product sample was obtained. The peptide was applied on silica gel column (100×1.5 cm), which had been equilibrated with a solvent mixture of n-BuOH:HOAc:H$_2$O=4:1:2, and then eluated with the same solvent system. Fractions of 3 ml were collected. Fractions 105-120 were combined and lyophilized; yield, 100 mg.

Amino Acid Analysis. The automatic amino acid analysis were performed on a Beckman Model 119 Automatic amino acid analyzer. The peptide was hydrolyzed for 24 hrs in a sealed glass tube at 110° C. in 6N HCl. The mixture was then dried, in vacuo. The residue was dissolved in 1.5 ml of sodium citrate buffer, pH 2.2 and 0.2 ml of the solution was applied to the analyzer.

Glu 1.976(2), Pro 2.039(2); Leu 1.986(2); Phe 0.990(1); Lys 1.003(1); Arg 1.000(1); NH$_3$(+); Trp(+).

High Pressure Liquid Chromatography. HPLC was performed on a Waters liquid chromatograph equipped with a Waters 660 solvent programmer. The samples was chromatographed on a μ-Bondapak C$_{18}$ (5μ) column (3.9×300 mm). For elution of the peptide, a linear gradient from 20-100% of solvent B in 25 min. was used (solvent A: 0.1 potassium phosphate buffer, pH 3.0; solvent B; 30% solvent A, 70% CH$_3$CN). The flow rate was 2 ml/min., 10 μl of a 0.1% solution of the peptide was injected. The eluted peptide was detected by its UV-absorbance at 206 nm. The retention time of the peptide was 14.5 min. and the purity was 98%.

Optical Rotation. Optical rotation, [α]$_D$, was measured at room temperature with a Perkin Elmer 141 polarimeter. The peptide was dissolved in 12% HOAc (5 mg/ml). [α]$_D$=−67.8.

TLC. Thin layer chromatography in 5 solvent systems: (1) n-BuOH:HOAc:H$_2$O=4:1:2, Rf 0.25; (2) n-BuOH:Pry:HOAc:H$_2$O=30:30:6:2:4, Rf 0.58; (3) n-BuOH:EtOAc:HOAc:H$_2$O=2:2:1:1, Rf 0.01; (4) EtOAc:Pyr:HOAc:H$_2$O=5:5:1:3, Rf 0.59; (5) n-BuOH:Pyr:HOAc:H$_2$O=50:30:1:40, Rf 0.54.

ABBREVIATIONS AND FORMULAS n-BuOH: n-butyl alcohol
HOAc: acetic acid
CH$_3$Cn: acetonitrile
K H$_2$PO$_4$: potassium phosphate
o-Cl-Z: o-chlorobenzyloxycarbonyl
CH$_2$Cl$_2$: dichloromethane
TFA: trifluoroacetic acid
Et$_3$N: triethylamine
DCC: dicyclohexylcarbodiimide
DMF: dimethylformamide i-PrOH: isopropyl alcohol
BOC: t-butyloxycarbonyl
COF$_3$: cobalt (III) fluoride
HF: hydrogen fluoride
EtOAc: ethyl acetate Characterization data on the analogs of substance P from which evolved the invention are in Tables I, II and III.

The sequence of substance P (SP) is expressed in the top of Table IV. The antagonistic activity is defined as the fold-increase in the concentration of SP in the presence of the analog to give 50% of the maximal response which is elicited by SP alone. The sequences of the analogs which were designed and synthesized are in Table IV. The eleven amino acids of SP are spaced across the top line to facilitate visual comparison of the amino acids in SP with those in the analogs. For exam-

TABLE I

Characterization Data on the Analogs of Substance P
Substance P: Arg—Pro—Lys—Pro—Gln—Gln—Phe—Phe—Gly—Leu—Met—NH$_2$

| Analog | I | II | III | IV | V |
|---|---|---|---|---|---|
| I. [D-Phe$^5$,D-Trp$^7$,D-Trp$^9$,Leu$^{11}$]—SP | 0.56 | 0.81 | 0.86 | 0.81 | 0.92 |
| II. [D-Arg$^1$,D-Pro$^2$,D-Phe$^5$,D-Trp$^7$,D-Trp$^9$,Leu$^{11}$]—SP | 0.92 | 0.04 | 0.61 | 0.37 | 0.25 |
| III. [Glp$^5$,D-Trp$^7$,D-Trp$^9$,Thr$^{11}$]—SP$_{5-11}$ | 0.91 | 0 | 0.53 | 0.25 | 0.17 |
| IV. [D-Arg$^1$,D-Pro$^2$,D-Trp$^7$,D-Trp$^9$,Thr$^{11}$]—SP | 0.93 | 0.01 | 0.52 | 0.28 | 0.22 |
| V. [Glp$^5$,D-Trp$^7$,D-Trp$^9$,Leu$^{11}$]—SP$_{5-11}$ | 0.93 | 0.84 | 0.87 | 0.67 | 0.76 |
| VI. [D-Arg$^1$,D-Trp$^7$,D-Trp$^9$,Leu$^{11}$]—SP | 0.58 | 0.01 | 0.59 | 0.54 | 0.25 |
| VII. [D-Arg$^1$,D-Pro$^2$,D-Trp$^7$,D-Trp$^9$,Leu$^{11}$]—SP | 0.82 | 0 | 0.54 | 0.28 | 0.20 |
| IX. [D-Trp$^7$,D-Trp$^9$,Leu$^{11}$]—SP | 0.82 | 0 | 0.57 | 0.35 | 0.18 |
| X. [D-Arg$^1$,D-Trp$^7$,D-Trp$^9$,Ile$^{11}$]—SP | 0.89 | 0 | 0.56 | 0.29 | 0.27 |
| XI. [D-Arg$^1$,D-Trp$^7$,D-Trp$^9$,Nle$^{11}$]—SP | 0.67 | 0 | 0.63 | 0.38 | 0.28 |

*I, EtOAc:py:HOAc:H$_2$O (5:5:1:3); II, n-BuOH:EtOAc:HOAc:H$_2$O (2:2:1:1); III, n-BuOH:py:HOAc:H$_2$O (30:30:6:24); IV, n-BuOH:py:HOAc:H$_2$O (50:33:1:40); V, n-BuOH:HOAc:H$_2$O (4:1:2)

TABLE II

Characterization Data on the Analogs of Substance P

| Analog | Retention time in HPLC (min.) | % Purity (HPLC) ca. | [α]$_D$ |
|---|---|---|---|
| I | 17.5 | 98 | +38.4** |
| II | 16 | 97 | −27* |
| III | — | — | +52** |
| IV | 14.5 | 96 | +38.6* |
| V | — | — | — |
| VI | 14.5 | 98 | −67.8* |
| VII | 14 | 96 | −50.4* |
| VIII | 16.5 | 95 | −38.7* |
| IX | 15 | 97 | −36.7* |
| X | 17.5 | 97 | −61.8* |
| XI | | | |

*C 0.5%, 15% HOAc
**C 0.5%, HOAc

TABLE III

Characterization Data on the Analogs of Substance P
Amino Acid Analytical Data

I. Glu 2.11(2); Leu 1.98(2); Phe 0.98*1); Trp (+).
II. Glu 0.93(1); Pro 1.98(2); Leu 2.06(2); Phe 2.00(2); Lys 1.03(1); Arg 1.00(1); NH$_3$ (+); Trp (+).
III. Glu 2.20(2); Thr 1.11(1); Leu 1.03(1); Phe 0.97(1); NH$_3$ (+); Trp (+).
IV. Glu 1.98(2); Pro 2.04(2); Thr 0.94(1); Leu 1.02(1); Phe 0.98(1); Lys 1.13(1); Arg 0.97(1); NH$_3$ (+); Trp (+).
V. Glu 2.06(2); Phe 0.95(1); Leu 2.00(2); Trp (+).
VI. Glu 1.98(2); Pro 2.04(2); Leu 1.99(2); Phe 0.99(1); Lys 1.00(1); Arg 1.00(1); NH$_3$ (+); Trp (+).
VII. Glu 1.99(2); Pro 2.04(2); Leu 2.07(2); Phe 0.98(1); Lys 0.96(1); Arg 0.96(1); NH$_3$ (+); Trp (+).
VIII. Glu 1.96(2); Pro 2.12(2); Leu 2.01(2); Phe 0.95(1); Lys 1.00(1); Arg 0.96(1); NH$_3$ (+); Trp (+).
IX. Glu 1.98(2); Pro 2.35(2); Leu 1.97(2); Phe 0.96(1); Lys 0.97(1); Arg 0.93(1); NH$_3$ (+); Trp (+).
X. Glu 1.01(2); Pro 1.02(2); Ile 0.91(1); Leu 1.02(1); Phe 0.97(1); Lys 1.03(1); Arg 1.02(1); NH$_3$ (+); Trp (+).

CHEMICAL AND BIOLOGICAL RESULTS

The antagonistic activities of the analogs were evaluated using the terminal portion of the guinea pig ileum, as described by Yamaguchi et al. [Acta Chem. Scand. B33, 63 (1979)]. The biological assay data are in Table IV.

ple, analog I is also spaced across the page to show the sequence relationship to SP. On this basis, analog I is H-Arg$^1$,Pro$^2$,Lys$^3$,Pro$^4$,D-Phe$^5$,Gln$^6$,D-Trp$^7$,Phe$^8$D-Trp$^9$,Leu$^{10}$,Leu$^{11}$-NH$_2$, but on the basis of conventional peptide nomenclature, analog I is expressed as [D-Phe$^5$,D-Trp$^7$,D-Trp$^9$,Leu$^{11}$]-SP$_{5-11}$.

The truncated heptapeptide I required a >200-fold increase at 10$^{-4}$ in the concentration of SP to allow 50% of the maximal response of SP. When D-Arg$^1$,D-Pro$^2$- were substituted for Arg$^1$,Pro$^2$- to give the undecapeptide II corresponding to I in positions 5–11, the activity was decreased, as revealed by the 64-fold and >200-fold increase, respectively.

The truncated heptapeptide III had a low antagonistic activity of 2-fold at 10$^{-4}$, and the corresponding undecapeptide, IV, with D-Arg$^1$,D-Pro$^2$- had an increased antagonistic activity of 5-fold at 10$^{-4}$.

The truncated heptapeptide V required at 17-fold increase at 10$^{-4}$ and the undecapeptide IX with the same sequence in positions 1–4, as in SP, required a 34-fold increase at 10$^{-4}$. Consequently, for this matching pair, the undecapeptide was twice as potent as the matching heptapeptide. When L-Arg$^1$ of the undecapeptide IX was changed to D-Arg$^1$, as in the undecapeptide VI, the antagonistic activity was significantly increased from 34-fold to 625-fold. When L-Pro$^2$ of the undecapeptide IX was changed to D-Pro$^2$ in the undecapeptide VIII, the antagonistic activity was increased two-fold from 34-fold to 70-fold at $10^{-4}$. When L-Arg$^1$ in the undecapeptide VIII was changed to D-Arg$^1$ as in the undecapeptide VII, the antagonistic activity was again increased from 70-fold to 100-fold at $10^{-4}$. Alternatively, when L-Pro$^2$ of the undecapeptide VI was changed to D-Pro$^2$ in the undecapeptide VII, the antagonistic potency was decreased from 625-fold to 100-fold at $10^{-4}$.

Evaluation of the antagonistic potencies of the four undecapeptides, VI-IX, shows that it is significantly beneficial to have the D-configuration of Arg in position 1 of SP for an antagonist, but to retain the L-configurations of Pro$^2$,Lys$^3$,Pro$^4$ in this N-terminal sequence of four amino acids in SP.

more active than the corresponding heptapeptide V by the potencies of 34-fold and 17-fold, respectively.

Uses for antagonists of substance P may be multiple; for example, the use of an antagonist for inflammatory responses in the human eye might be better with an undecapeptide, but uses of truncated antagonists might be fully satisfactory for analgesic action in an intact mammalian species.

These undecapeptides and truncated peptides which are based on the sequence of substance P, but which have antagonistic activity rather than agonistic activity, have several uses. The availability of such an antagonist like [D-Arg$^1$,D-Trp$^7$,D-Trp$^9$,Leu$^{11}$]-Sp makes possible the elucidation of the mechanisms of multiply biological actions of substance P, which is quite impossible in the absence of such antagonists. Since substance P itself is apparently a neurogenic mediator of the inflammatory response in the human eye, this antagonist of substance P is useful in ophthalmology to therapeutically treat

TABLE IV
Biological Assay Data for Antagonism

| | | | | | | | | | | Fold increase in conc. |
|---|---|---|---|---|---|---|---|---|---|---|
| (SP) | H—Arg$^1$ | Pro$^2$ Lys$^3$Pro$^4$ | Gln$^5$ Gln$^6$ | Phe$^7$ Phe$^8$ | Gly$^9$ Leu$^{10}$ | Met$^{11}$NH$_2$ | | | | |
| I. | [ | | D-Phe$^5$ | D-Trp$^7$ | D-Trp$^9$ | Leu$^{11}$]—SP$_{5-11}$ | | | | 200/10$^{-4}$* |
| II. | [D-Arg$^1$ | D-Pro$^2$ | D-Phe$^5$ | D-Trp$^7$ | D-Trp$^9$ | Leu$^{11}$]—SP | | | | 64/10$^{-4}$ |
| | | | | | | | | | | 7/10$^{-5}$ |
| III. | [ | | Glp$^5$ | D-Trp$^7$ | D-Trp$^9$ | Thr$^{11}$]—SP$_{5-11}$ | | | | 2/10$^{-4}$ |
| IV. | [D-Arg$^1$ | D-Pro$^2$ | | D-Trp$^7$ | D-Trp$^9$ | Thr$^{11}$]—SP | | | | 5×/10$^{-4}$ |
| V. | [ | | Glp$^5$ | D-Trp$^7$ | D-Trp$^9$ | Leu$^{11}$]—SP$_{5-11}$ | | | | 17×/10$^{-4}$ |
| VI. | [D-Arg$^1$ | | | D-Trp$^7$ | D-Trp$^9$ | Leu$^{11}$]—SP | | | | 625/10$^{-4}$ |
| VII. | [D-Arg$^1$ | D-Pro$^2$ | | D-Trp$^7$ | D-Trp$^9$ | Leu$^{11}$]—SP | | | | 100/10$^{-4}$ |
| | | | | | | | | | | 17/10$^{-5}$ |
| VIII. | [ | D-Pro$^2$ | | D-Trp$^7$ | D-Trp$^9$ | Leu$^{11}$]—SP | | | | 70/10$^{-4}$ |
| | | | | | | | | | | 13/10$^{-5}$ |
| IX. | [ | | | D-Trp$^7$ | D-Trp$^9$ | Leu$^{11}$]—SP | | | | 34/10$^{-4}$ |

*difficulty soluble in 50% ethanol.

For two pairs of heptapeptides and undecapeptides having relatively low antagonistic activities, the undecapeptides had somewhat higher antagonistic activities. When an undecapeptide of high antagonistic activity (625-fold at $10^{-4}$) is compared with the corresponding heptapeptide, it is the undecapeptide which is significantly more potent. Since it is the antagonist of high potency which is important for physiological research, the undecapeptide is more important than the truncated heptapeptide.

These results indicate that the N-terminal Arg$^1$,-Pro$^2$,Lys$^3$,Pro$^4$ are apparently very important for binding at a receptor even though these four amino acids may not be directly involved in mechanisms in agonism. Although the heptapeptide has antagonistic activity, the use of the undecapeptide in physiology may better reveal intrinsic mechanisms, i.e., the heptapeptide might reveal more artifactual relationships.

The fact that Arg$^1$ has the D- rather than the natural configuration in VI indicates possible greater enzymic stability. The superiority of D-Arg$^1$ over L-Arg$^1$ for both undecapeptides, VI and VII, is revealed by the increases to 625-fold and 100-fold, respectively, at $10^{-4}$ in comparison with IX and VIII at 34-fold and 70-fold, respectively.

These pairs of heptapeptides and undecapeptides show that a heptapeptide is not necessarily as antagonistically potent as the corresponding undecapeptide, but rather that undecapeptides may be more active than the corresponding heptapeptides. The undecapeptide IX is inflammatory responses in the human eye, and the therapeutic application may be topical, which is very practical. Another use involves the action of such an antagonist to block substance P in pain mechanisms, and on this basis the antagonist has a useful analgesic action.

The several examples of antagonists of substance P set forth in this document exemplify a category of analogs which have useful and potent antagonistic activity. It is obvious that other substituents in the positions of the undecapeptides and truncated peptides, which are clearly based on the structures of the disclosed peptides, are entirely within the scope of this invention.

What is claimed:
1. [D-Arg$^1$,D-Trp$^7$,D-Trp$^9$,Leu$^{11}$]-Sp.
2. [D-Phe$^5$,D-Trp$^7$,D-Trp$^9$,Leu$^{11}$]-SP$_{5-11}$.
3. Substance P having amino acid substitutions at one or more of positions 1, 2, 5, 7, 9, or 11, wherein the amino acid substitution at position 1 is D-Arg; position 2 is D-Pro; position 5 is D-Phe; position 7 is D-Trp; position 9 is D-trp; and position 11 is Leu.
4. The substituted Substance P of claim 3 which is [D-Arg$^1$, D-Pro$^2$, D-Phe$^5$, D-Trp$^7$, D-Trp$^9$, Leu$^{11}$]-SP.
5. The substituted Substance P of claim 3 which is [D-Arg$^1$, D-Pro$^2$, D-Trp$^7$, D-Trp$^9$, Leu$^{11}$]-SP.
6. The substituted Substance P of claim 3 which is [D-Pro$^2$, D-Trp$^7$, D-Trp$^9$, Leu$^{11}$]-SP.
7. The substituted Substance P of claim 3 which is [D-Trp$^7$, D-Trp$^9$, Leu$^{11}$]-SP.

* * * * *